United States Patent [19]

Druin et al.

[11] 3,943,175

[45] Mar. 9, 1976

[54] SYNTHESIS OF PURE 3,3'-DIAMINOBENZIDINE

[75] Inventors: Melvin L. Druin, West Orange, N.J.; Kenneth Oringer, Westport, Conn.

[73] Assignee: Celanese Corporation, New York, N.Y.

[22] Filed: Mar. 9, 1973

[21] Appl. No.: 339,910

Related U.S. Application Data

[63] Continuation of Ser. No. 868,198, Oct. 21, 1969, abandoned.

[52] U.S. Cl. ............................... 260/581; 260/582
[51] Int. Cl.² ................... C07C 85/26; C07C 85/04
[58] Field of Search ............................ 260/581, 582

[56] References Cited
UNITED STATES PATENTS

| | | | |
|---|---|---|---|
| 1,607,824 | 11/1926 | Hale et al. | 260/581 |
| 2,036,134 | 3/1936 | Graenacher et al. | 260/581 X |
| 2,149,525 | 3/1939 | Jenkins | 260/582 |
| 2,194,938 | 3/1940 | Henke et al. | 260/582 X |
| 3,358,025 | 12/1967 | Foster et al. | 260/582 X |
| 3,480,673 | 11/1969 | Smith | 260/581 X |

FOREIGN PATENTS OR APPLICATIONS

| | | | |
|---|---|---|---|
| 1,475,631 | 4/1967 | France | 260/581 |

*Primary Examiner*—Elbert L. Roberts
*Assistant Examiner*—S. P. Williams

[57] ABSTRACT

A process for the purification of crude 3,3'-diaminobenzidine comprising contacting it with sulfuric acid. The 3,3'-diaminobenzidine can be produced by the reaction of $NH_3$ and 3,3'-dichlorobenzidine in the presence of various catalysts.

10 Claims, No Drawings

3,943,175

SYNTHESIS OF PURE 3,3'-DIAMINOBENZIDINE

This is a continuation of application Ser. No. 868,198, filed Oct. 21, 1969, now abandoned.

BACKGROUND OF THE INVENTION

The synthesis of 3,3'-diaminobenzidine hereinafter DAB by the ammonolysis of 3,3'-dichlorobenzidine, hereinafter DCB, is known in the art as described in French patent No. 1,475,631 (1967). Unfortunately, the above and other prior processes suffer from a number of disadvantages such as the resultant impure reaction products which comprise DAB, DCB, and catalysts when such are employed in the synthesis.

SUMMARY OF THE INVENTION

Accordingly, it is an object of the present invention to provide a novel process for the synthesis of DAB which is substantially free of one or more of the disadvantages of prior processes.

Another object is to provide a novel process for the synthesis of DAB of greater purity than heretofore possible.

A further object is to provide a novel process for the removal of DCB and/or catalyst residues present as contaminants in crude DAB.

Additional objects and advantages of the present invention will be apparent to those skilled in the art by reference to the following detailed description thereof.

The above and other objects are accomplished according to the present invention by contacting or leaching the crude DAB with sulfuric acid.

DETAILED DESCRIPTION OF PREFERRED EMBODIMENTS

The synthesis of crude DAB is conducted by reacting DCB with ammonia preferably in the presence of a catalyst. The catalyst may comprise a copper halide. For example, the catalyst may comprise copper and cuprous chloride wherein the molar ratio of copper to cuprous chloride is up to 4:1, for example 0.5:1 to 3:1. In the presence of water, the cuprous chloride catalyst may be present as copper ions and chloride ions. The reacting is accomplished by contacting the reactants and the catalyst under any conditions that will form DAB and generally by charging these to a reaction zone in any suitable vessel such as an autoclave.

The reaction temperature is not critical, the reaction being conducted at any temperature above which the reaction proceeds at an economic rate and below which undesirable competing reactions take place. Examples of undesirable competing reactions include thermal degradation of the reactants or products; hydrolysis of the DCB to an undesirable ammonium derivative and/or reaction of DCB with DAB to form undesirable secondary and tertiary amines. The temperature is generally between 100° and 500°C and preferably between 175° and 300°C. The pressure likewise is not critical however super-ambient pressures are preferred since they tend to drive the reaction to completion. The reaction pressure is generally between 10 and 10,000 psig and preferably between 500 and 2,500 psig. In a preferred embodiment of the present invention the reaction is conducted at autogenous pressure. The reaction is conducted until the desired amount of DCB has been converted to DAB. If it is desired that the reaction go to completion such can be determined by any convenient means such as melting point tests conducted on a differential scanning calorimeter or any other convenient means. Completion of the reaction is usually observed in 2 to 8 hours.

By ammonia is meant any $NH_3$ releasing substance preferred examples of which include ammonium hydroxide, gaseous or liquid $NH_3$ and mixtures thereof such as aqua ammonia. The reaction is preferably conducted in the presence of some water supplied to the reaction zone as such or in the form of ammonium hydroxide. The $NH_3$ is preferably present in a stoichiometric excess over that necessary to completely convert DCB to DAB and is generally present in a molar ratio of 2:1 to 200:1 and preferably 10:1 to 60:1 and most preferably 15:1 to 30:1. The molar ratio of cuprous chloride in the catalyst to DCB is 1:10 to 5:10, for example, 1:10 to 3:10.

Further according to the present invention, it has been discovered that impurities can be leached from impure DAB by the use of sulfuric acid. The sulfuric acid can simply be passed through the solid crude impure DAB, or the impure DAB can be mixed with the sulfuric acid followed by filtration wherein the impurities are removed in the filtrate. It has been found that such leaching process is effective to remove copper chlorides such as cuprous chloride and cupric chloride and is also effective to separate unreacted DCB from DAB. In an especially preferred process, the impure DAB which can be a mixture of DAB and copper chlorides and/or unreacted DCB is contacted with sulfuric acid to form a slurry. This slurry is then filtered to remove the impurites as filtrate leaving behind a filter cake substantially free of impurities.

Widely varying strengths of sulfuric acid can be employed and generally from volume concentrations of 0.1% up to 75%, and preferably from 2 to 35%. The contacting of the sulfuric acid with the impure DAB can be conducted in a variety of processes such as by forming a slurry of the two or by simply placing the impure DAB on a filter paper and passing the sulfuric acid through the impure DAB. The contacting can be conducted in a single step or in multiple steps, but the preferred method is to mix the impure DAB with sulfuric acid of the preferred concentration present in an amount such that there is stoichiometric excess of sulfuric acid over that necessary to convert all DAB to DAB hydrosulfate which generally occurs within a period of from 20 minutes to 2 hours.

The contacting can take place at widely varying temperatures and generally from −10°C to 120°C, but preferably from 20° to 50°C. These same temperatures apply for the filtering step when such is conducted separately. In general, temperatures and concentrations above those specified are undesirable since they tend to cause substitution of the DAB producing undesirable amino-sulfonic acids.

After filtering, the acid treated reaction products are treated with a base to reconvert the DAB hydrosulfate to DAB. In general, any strong or weak base can be employed which will react with the DAB hydro-sulfate and reconvert it to DAB. Examples of suitable bases include among others sodium hydroxide, sodium carbonate and ammonia. A base is added until all of the acid is neutralized which generally occurs by the time the neutralization mixture exhibits a pH of 6 to 8, and preferably about 7.

While it is not desired to limit the present invention to any theory, the following is offered by way of possible explanation. During the catalytic synthesis of DAB, a DAB-copper halide complex apparently forms. During the contacting step with sulfuric acid, the $H_2SO_4$ apparently displaces the copper halide from the complex and forms the acid insoluble DAB hydrosulfate, i.e. 3,3'-diaminobenzidine.$4H_2SO_4$. The DAB cupric halide complex is apparently less reactable with sulfuric acid than is the cuprous halide complex. Therefore, higher purities can be achieved by means of the leaching process when the copper halide consists essentially of cuprous halide. For this reason the preferred catalysts to be employed in conjunction with the leaching step are catalysts of copper and cuprous halide. The presence of copper tends to reduce any cupric halide which may form to the cuprous state, thus producing a DAB complex which is more easily reacted with the sulfuric acid. Apparently the sulfuric acid also forms a complex with the unreacted DCB, however, under the preferred conditions of temperature and acid concentration, a large difference in solubilities is observed between DCB hydrosulfate and DAB hydrosulfate facilitating their separation.

Since pure DAB contains a stoichiometric amount of nitrogen but no chlorine and no copper, the purity of the final product can be determined by elemental analysis for chlorine, nitrogen and/or copper. Chlorine can be present due to DCB, $NH_4Cl$, or from the catalyst. When DCB is present nitrogen analysis (Kjeldahl) is preferably used to establish purity, assuming that the crude produce is a binary mixture of DCB and DAB. The presence of copper is generally attributed to the catalyst.

The molar ratio of cuprous chloride to DCB is not critical but optimum results occur at molar ratios of 0.1:10 to 5:10 and preferably 1:10 to 3:10 moles cuprous chloride per mole DCB.

By ammonia is meant any $NH_3$ releasing substance preferred examples of which include ammonium hydroxide, gaseous or liquid $NH_3$ and mixtures thereof such as aqua ammonia. The reaction is preferably conducted in the presence of some water supplied to the reaction zone as such or in the form of ammonium hydroxide. The $NH_3$ is preferably present in a stoichiometric excess over that necessary to completely convert DCB to DAB and is generally present in a molar ratio of 2:1 to 200:1 and preferably 10:1 to 60:1 and most preferably 15:1 to 30:1.

DAB is a known compound of well known utility and is useful as an intermediate in the synthesis of high temperature resistant polymers such as poly-2,2'-(m-phenylene)-5,5'-bibenzimidazole as described in U.S. Pat. Nos. 2,895,948 and 3,174,947. DAB is also useful as an antioxidant and as a curing agent for epoxy resins.

The following examples are given as specific illustrations of the invention. It should be understood, however, that the invention is not limited to the specific details set forth in the examples.

EXAMPLE 1

This example illustrates the ammonolysis of DCB using a $Cu_2Cl_2$ catalyst and an NH:DCB ratio of 15:1.

An autoclave is charged with 532 gm of DCB, 83.4 gm of $Cu_2Cl_2$ and 2000 ml of ammonium hydroxide containing 30 weight percent $NH_3$ to form a slurry. The slurry is heated to and maintained at 225° C and 900 psig for a period of 4 hours. The crude reaction product is cooled, filtered washed with water, dried, and found to weigh 436 gm of which 372 gm are DAB corresponding to a yield of 82.4% of theory. The purity of the crude product is 85.3% DAB.

The purity is calculated by the formula:

$$\text{Purity} = \frac{(N)}{(26.17)} 100$$

wherein N is the weight percent of elemental nitrogen in the sample determined for example by the Kjeldahl method.

EXAMPLE 2

This example illustrates the ammonolysis of DCB using a copper plus $Cu_2Cl_2$ catalyst and an $NH_3$:DCB ratio of 15:1.

An autoclave is charged with 513 gm of DCB, 25.8 gm of granulated copper which passes through a U.S. standard screen of 10 mesh per inch and is retained on a screen of 600 mesh per inch, 40.1 gm of $Cu_2Cl_2$ and 2000 ml of ammonium hydroxide containing 28.8 weight percent $NH_3$ to form a slurry. The slurry is heated to and maintained at 225° C and 900 psig for a period of 4 hours. The crude reaction product is cooled, filtered, washed with water, dried, and found to weigh 440 gm of which 381.0 gm are DAB corresponding to a yield of 86.6% of theory. The purity of the crude product is 84.5% DAB calculated as in Example 1.

EXAMPLE 3

This example illustrates the process of the present invention and indicates the recoveries and elemental analyses of crude DAB, acid-leached DAB, and leached recrystallized DAB.

The crude product of Example 1 is analyzed and the results recorded in Table I as Run No. 1; the elemental analyses results being recorded in columns 2 through 8, and the melting point in column 9.

This crude product (10 gm) is placed in a flask along with sulfuric acid (90 ml, 15 vol.%) and agitated for 1 ½ hours. The contents of the flask are then placed on filter paper in a Buchner funnel, washed once with sulfuric acid (33 ml, 15 vol.%), and once with water (90 ml). The resultant filter cake is placed in a flask, whereupon sodium carbonate solution (253 ml, 10 wt. % $Na_2CO_3$) is added slowly to avoid excessive foaming. The flask and its contents are then cooled to 18° C, filtered, water washed, and dried in vacuo overnight at 100° C.

A second analysis of the product is conducted, and the results entered in Table I in columns 2 through 9 as Run No. 2.

The product is then dissolved in boiling water (520 ml) to which has been added charcoal (3.12 gm), commercially available as Darco, and diatomaceous earth (1.17 gm) commercially available as Celite. Insolubles are removed by filtration, and the filtrate containing DAB permitted to cool, whereupon DAB crystallized out. The product is dried in vacuo overnight at 100° C, analyzed a third time, and the results recorded in Table I as Run No. 3. Theoretical values are recorded in as Run No. 4 for comparative purpose.

Table I

| 1. Run (No.) | Elemental Analysis | | | | | | | 9. Melting Point |
|---|---|---|---|---|---|---|---|---|
| | 2. N (%) | 3. Cl (%) | 4. Cu (%) | 5. S (%) | 6. Na (%) | 7. C (%) | 8. H (%) | |
| 1 | 22.3 | 4.57 | 5.29 | — | — | 60.2 | 6.16 | 151–170[1] 172–189[2] |
| 2 | 24.1 | 0.01 | .55 | 0.12 | — | — | — | 159–172 |
| 3 | 26.4 | 0.003 | 0.008 | <0.01 | 0.001 | 66.3 | 6.42 | 175–179 |
| 4 (theory) | 26.17 | 0 | 0 | 0 | 0 | 67.29 | 6.54 | 179–182 |

[1]major peak
[2]minor peak

EXAMPLE 4

This example illustrates the purification of the crude product from Examples 1 and 2, and illustrates the increased recoveries by the acid-leach process of the present invention when applied to crude products produced by the ammonolysis of DCB in the presence of copper-$Cu_2Cl_2$ catalyst compared to that produced in the presence of a $Cu_2Cl_2$ catalyst alone.

Elemental analyses and melting point tests are conducted on the crude product of Example 3, and the results thereof entered in the first line of Columns 5 through 10 in Table II as Run No. 1. The crude product (30 g) is placed in a flask containing sulfuric acid (270 ml, 15 vol.%) and is mixed for 1 and one half hours. Contents of the flask are then placed on filter paper in a Buchner funnel, washed once with sulfuric acid (100 ml, 15 vol.%) and once with water (267cc). The resultant filter cake is then placed in a flask, whereupon aqueous sodium carbonate solution (760 ml, 10 wt. % $Na_2CO_3$) is added slowly. The flask and its contents are then cooled to 18° C, filtered, water washed, and dried overnight in vacuo at 100° C and found to weigh 23.4 gm corresponding to a recovery of 78.1 wt. % which is entered in column 3 of Table II.

The product is then dissolved in boiling water (1560 ml) to which has been added (9.36 gm) Darco and diatomaceous earth 3.51 gm Celite. Insolubles are removed by filtration and the filtrate containing DAB permitted to cool, whereupon DAB crystallizes out. The product is dried in vacuo overnight at 100° C, analyzed a third time, and the results recorded in Table II on the third line as Run No. 3. The weight recovered is 11.5 gm which corresponds to a final recovery (acid leach and recrystallization) of 38.4%.

EXAMPLE 5

The procedure of Example 4 is repeated employing the same times, temperatures, conditions, and ingredients except that the crude product from Example 1 is replaced by the crude product from Example 2, and the results thereof recorded in Table II as Runs 4 through 6.

TABLE II

| 1. Run (No.) | 2. Process Step | Recovery | | Elemental Analysis | | | | | 10. Melting Point (°C) |
|---|---|---|---|---|---|---|---|---|---|
| | | 3. After acid leach % | 4. After recrystallization % | 5. N % | 6. Cl % | 7. Cu % | 8. C % | 9. H % | |
| 1. | Crude | 100 | | 22.3 | 4.57 | 5.29 | 60.2 | 6.16 | 151–170 |
| 2. | Acid leach only | 78.1 | | 24.5 | 0.10 | 0.60 | — | — | 155–173 |
| 3. | Acid leach and recrystallization | | 38.4 | 25.6 | 0.02 | 0.03 | — | — | 177–181 |
| 4. | Crude | 100 | | 22.3 | 5.74 | 4.19 | 61.6 | 5.94 | 158–173 |
| 5. | Acid leach only | 78.0 | | 23.8 | 0.07 | 0.86 | — | — | 165–173 |
| 6. | Acid leach and recrystallization | | 51.9 | 26.11 | 0.01 | 0.07 | 67.4 | 6.54 | 175–181 |
| Theory | — | — | — | 26.17 | 0 | 0 | 67.29 | 6.54 | 179–182 |

EXAMPLE 6

This example illustrates the removal of DCB from a mixture of DCB and DAB by leaching with sulfuric acid.

DAB, produced as described in Example 1, is analyzed and the results recorded in Table III as Run No. 1. DCB is likewise analyzed and the results recorded as Run No. 2. Then the amount of DAB shown in column 2 is mixed with the amount of DCB shown in column 3, and the resultant mixture analyzed and the results recorded as Run No. 3. The mixture is then mixed with sulfuric acid (900 ml, 15 wt.%) for 1 ½ hours in a flask. the contents of the flask are then placed on filter paper in a Buchner funnel, washed once with sulfuric acid (33 ml, 15 wt.%) and once with water (889 ml). The resultant filter cake is placed in a flask whereupon aqueous sodium carbonate solution (2530 ml, 10 wt. % $Na_2CO_3$) is added slowly to avoid excessive foaming attendant upon release of carbon dioxide from acid decomposition of the sodium carbonate. The flask and its contents are then cooled to 18°C, filtered, water washed, and dried overnight in vacuo at 100°C. Elemental analyses for chlorine and nitrogen are conducted, and the results recorded in column 4 and 5 as Run No. 4. The melting point is determined and recorded in column 7.

TABLE III

| 1. Run (No.) | Composition | | Elemental Analysis | | 6. Melting Point (°C) |
|---|---|---|---|---|---|
| | 2. DAB (g) | 3. DCB (g) | 4. Cl (%) | 5. N (%) | |
| 1. | 100 | 0 | 0.02 | 25.7 | 177–181 |
| 2. | 0 | 100 | 27.8 | 11.0 | 131–134 |
| 3. | 80 | 20 | 5.6 | 23.2 | — |
| 4. | 95.6 | 4.4 | 1.54 | 25.4 | 176–180 |

EXAMPLE 7

This comparative example illustrates the attempted purification of crude DAB by the use of hydrochloric acid.

Crude DAB (10 g) from Example 1 was dissolved in hydrochloric acid (220 ml, 3.28 vol. %) to form a solution. This solution was filtered through a Buchner funnel and the DAB hydrochloride collected as the filtrate. The DAB was precipitated by adding concentrated hydrochloric acid until the final concentration of the mixture was 9.5 volume percent. The DAB hydrochloride precipitate is recovered by filtration. The filter cake is mixed with water, neutralized with sodium hydroxide, and dried in vacuo overnight at 100°C. The product is weighed, indicating a 62.9 weight percent recovery based upon the amount of DAB originally present in the crude product. An elemental analysis is conducted which indicates 23.8% nitrogen, 4.75% chlorine, and 1.00% copper. The melting point is 168°–173°C. As indicated by these results, the recovery is only 62.9, whereas the amount of chlorine and copper present is very high.

Although the invention has been described in considerable detail with reference to certain preferred embodiments thereof, it will be understood that variations and modifications can be effected within the spirit and scope of the invention as described above and as defined in the appended claims.

What is claimed is:

1. A process for the synthesis of substantially pure 3,3'-diaminobenzidine from 3,3'-dichlorobenzidine consisting essentially of the sequential steps of:
    I. reacting 3,3'-dichlorobenzidine with NH₃ in the presence of a catalyst consisting essentially of a copper chloride to form a crude reaction product;
    II. mixing the crude reaction product with a stoichiometric excess of sulfuric acid to convert the 3,3'-diaminobenzidine to acid-insoluble 3,3'-diaminobenzidine hydrosulfate with the remainder of the reaction product being substantially dissolved;
    III. filtering the reaction product and thereby recovering the 3,3'-diaminobenzidine hydrosulfate as filter cake; and
    IV. contacting the filter cake with a base to reconvert the solid 3,3'-diaminobenzidine hydrosulfate to 3,3'-diaminobenzidine.

2. A process for the synthesis of substantially pure 3,3'-diaminobenzidine from 3,3'-dichlorobenzidine consisting essentially of the sequential steps of:
    I. reacting 3,3'-dichlorobenzidine with NH₃ at 100° to 500°C. at a pressure of 10 to 10,000 psig in the presence of a catalyst consisting essentially of copper and cuprous chloride to form a crude reaction product; wherein the molar ratio of copper to cuprous chloride is up to 4:1; wherein the molar ratio of cuprous chloride to 3,3'-dichlorobenzidine is 1:10 to 5:10; and wherein the molar ratio of NH₃ to 3,3'-dichlorobenzidine is 10:1 to 60:1;
    II. mixing the crude reaction product with a stoichiometric excess of 0.1 to 75 vol. % sulfuric acid at −10° to 120°C. to convert the 3,3'-diaminobenzidine to acid-insoluble 3,3'-diaminobenzidine hydrosulfate with the remainder of the reaction product being substantially dissolved;
    III. filtering the reaction product and thereby recovering the 3,3'-diaminobenzidine hydrosulfate as filter cake; and
    IV. contacting the filter cake with a base to reconvert the 3,3'-diaminobenzidine hydrosulfate to 3,3'-diaminobenzidine.

3. A process of claim 1 for the synthesis of substantially pure 3,3'-diaminobenzidine from 3,3'-dichlorobenzidine consisting essentially of the sequential steps of:
    I. reacting 3,3'-dichlorobenzidine with NH₃ at 175° to 300°C. and autogenous pressure in the presence of water and a catalyst consisting essentially of finely divided copper and cuprous chloride to form a crude reaction product; wherein the molar ratio of copper to cuprous chloride is 0.5:1 to 3:1; wherein molar ratio of cuprous chloride to 3,3'-dichlorobenzidine is 1:10 to 3:10; and wherein the molar ratio of NH₃ to 3,3'-dichlorobenzidine is 15:1 to 30:1;
    II. mixing the crude reaction product with a stoichiometric excess of 2 to 35 volume per cent sulfuric acid at 20° to 50°C. to convert the 3,3'-diaminobenzidine to acid-insoluble 3,3'-diaminobenzidine hydrosulfate;
    III. filtering the reaction product and thereby recovering the 3,3'-diaminobenzidine hydrosulfate as filter cake;
    IV. contacting the filter cake with a base to reconvert the 3,3'-diaminobenzidine hydrosulfate to 3,3'-diaminobenzidine;
    V. dissolving the 3,3'-diaminobenzidine in boiling water to form a hot solution;
    VI. filtering the hot solution to remove copper and any other insoluble contaminants; and
    VII. cooling the hot solution to crystallize the 3,3'-diaminobenzidine.

4. In a process for producing 3,3'-diaminobenzidine by the ammonolysis of 3,3'-dichlorobenzidine in the presence of ions of copper and ions of chloride, the improvement wherein the unreacted 3,3'-dichlorobenzidine, the ions of copper and the ions of chlorine are leached from the ammonolysis reaction products by sulfuric acid leaving a product consisting essentially of acid-insoluble 3,3'-diaminobenzidine hydrosulfate substantially free of 3,3'-dichlorobenzidine, ions of copper and ions of chlorine.

5. A process for separating 3,3'-diaminobenzidine from impure 3,3'-diaminobenzidine formed by the ammonolysis of 3,3'-dichlorobenzidine in the presence of a copper halide catalyst, which process consists essentially of the steps of leaching the impurities from the said impure 3,3'-diaminobenzidine by contacting the said impure 3,3'-diaminobenzidine with sulfuric acid whereby acid-insoluble 3,3'-diaminobenzidine hydrosulfate is formed and the said impurities are dissolved, and separating the solid 3,3'-diaminobenzidine hydrosulfate from the dissolved impurities.

6. The process of claim 5 wherein the sulfuric acid has a concentration of 2 to 35 volume percent.

7. the process of claim 5 wherein the copper halide is cupric chloride.

8. The process of claim 5 wherein the copper halide is cuprous chloride.

9. The process of claim 5 wherein said solid 3,3'-diaminobenzidine is separated by filtering.

10. The process of claim 9 wherein the said filtering is conducted at a temperature of 20° to 50°C.

* * * * *